(12) United States Patent
Chapon

(10) Patent No.: US 7,227,635 B2
(45) Date of Patent: Jun. 5, 2007

(54) DEVICE AND METHOD FOR POSITIONING A SAMPLE MOUNTED ON A GLOW DISCHARGE SPECTROMETER

(75) Inventor: Patrick Chapon, Villebon (FR)

(73) Assignee: Cabinet Harle & Phelip, Longjumeau (FR)

( * ) Notice: Subject to any disclaimer, the term of this patent is extended or adjusted under 35 U.S.C. 154(b) by 421 days.

(21) Appl. No.: 10/480,264

(22) PCT Filed: Jun. 17, 2002

(86) PCT No.: PCT/FR02/02083

§ 371 (c)(1),
(2), (4) Date: Jun. 7, 2004

(87) PCT Pub. No.: WO02/103336

PCT Pub. Date: Dec. 27, 2002

(65) Prior Publication Data

US 2004/0233427 A1   Nov. 25, 2004

(30) Foreign Application Priority Data

Jun. 18, 2001   (FR) .................................. 01 07986

(51) Int. Cl.
*G01J 3/30*   (2006.01)
*G01T 1/18*   (2006.01)

(52) U.S. Cl. ...................................... 356/311; 250/288
(58) Field of Classification Search ................ 33/277, 33/286; 356/311, 399

See application file for complete search history.

(56) References Cited

U.S. PATENT DOCUMENTS

| | | | | |
|---|---|---|---|---|
| 4,623,229 A | * | 11/1986 | Galan | 359/845 |
| 4,762,411 A | * | 8/1988 | Pitalo et al. | 356/152.3 |
| 4,912,324 A | * | 3/1990 | Clark et al. | 250/288 |
| 5,086,226 A | * | 2/1992 | Marcus | 250/288 |
| 5,172,183 A | * | 12/1992 | Mega et al. | 356/311 |

\* cited by examiner

*Primary Examiner*—Layla G. Lauchman
(74) *Attorney, Agent, or Firm*—Arent Fox LLP

(57) ABSTRACT

This invention relates to a device and a method for positioning a sample (8) mounted on a glow discharge spectrometer (6). A sample (8) to be analyzed is mounted on the first electrode means (5) of a glow discharge spectrometer (6) then a detachable arm (11) is mounted on a mechanic assembly comprising a cutting tool (2). This detachable arm (11) comprises a light source (14) used for illuminating said sample (8) with a light beam having a diameter equal to the inner diameter of the first electrode means (5) and then the position of the light beam is located on the sample (8). The portion of the sample (8) which will be exposed effectively to the glow discharge may thus be located with accuracy.

9 Claims, 2 Drawing Sheets

DEVICE AND METHOD FOR POSITIONING A SAMPLE MOUNTED ON A GLOW DISCHARGE SPECTROMETER

CROSS-REFERENCE TO RELATED APPLICATION

This application is a National Stage entry of International Application No. PCT/FR02/02083, the entire specification claims and drawings of which are incorporated herewith by reference.

This invention relates to a device and a method for positioning a sample installed on a glow discharge spectrometer.

Glow discharge spectrometry enables to establish the multi-elemental composition of a sample, conductive or non conductive on depths varying from a few nanometers to several hundred micrometers. This is a method for quick and direct analysis of solids, regardless whether they are in the form of metals, powders, polymers, ceramics or even glass. Glow Discharge Optical Emission Spectrometry includes a source with glow discharge and one or several optic spectrometers.

The sample to be analysed is placed generally manually on the spectrometer and its positioning occurs in a blind fashion. This difficult positioning of the sample is due to a lack of visibility of the zone of the spectrometer facing the anode. Consequently, locating, prior to analysing, the portion of the surface of the sample which will be exposed effectively to the glow discharge created in the spectrometer is difficult.

Such a spectrometer often includes a device enabling to clean anode after putting into service the glow discharge source. Indeed, in the operating principle of such a source, a gas, generally argon (with a pressure of the order of 5 mbar) is ionised and sputters the surface of the sample to be analysed. There results the ejection of atoms forming said sample which either are pumped, or cover the surfaces of the anode. The latter tends therefore to be covered with a deposit liable to degrade the operation of the source. It is thus necessary to eliminate such coating using a sharp tool, a drill bit for instance.

The purpose of this invention is to provide a device and a method, simple in their design and in their operating mode enabling accurate positioning of a sample on a glow discharge source while resorting to the device enabling to clean the anode.

To this end, the invention relates to a device for positioning a sample in a glow discharge spectrometer comprising a protective member of a mechanic assembly, said mechanic assembly including a cutting tool liable to receive a detachable arm having a main axis, said glow discharge spectrometer comprises first electrode means, of inner diameter D, against which a sample to be analysed may be mounted, said sample having a first face and a second face, said first face liable to be exposed partially to a glow discharge created in the spectrometer and the second face being external to said spectrometer and opposite the mechanic assembly, According to the invention:
the detachable arm includes a light source generating a light beam centered on said first electrode means.

This invention also relates to the features which will appear during the following description and which should be considered individually or in all their technically possible combinations:
the light beam has a diameter d substantially equal to the inner diameter D of the first electrode means,
the light source is a laser diode,
the light source is situated along the main axis of the arm,
the light source is located perpendicular to the main axis of the arm,
a mirror plan is inserted in the arm and positioned at 45° of the main axis of the arm,
the arm is fitted with an output optic lens.

The invention also relates to a method for positioning a sample in a glow discharge spectrometer.

According to the invention,
a sample to be analysed is installed against first electrode means of a glow discharge spectrometer,
a detachable arm is installed on a mechanic assembly comprising a sharp tool, said arm being centered and in the axis of the first electrode means,
said sample is illuminated with a light beam having a diameter d substantially equal to the inner diameter D of the first electrode means,
the position of the luminous beam is located on the sample.

This invention also relates to the features which will appear during the following description and which should be considered individually or in all their technically possible combinations:
the structure of the sample is mapped using the glow discharge spectrometer.

The invention will be described more in detail with reference to the appended drawings whereon:

Figure 1:
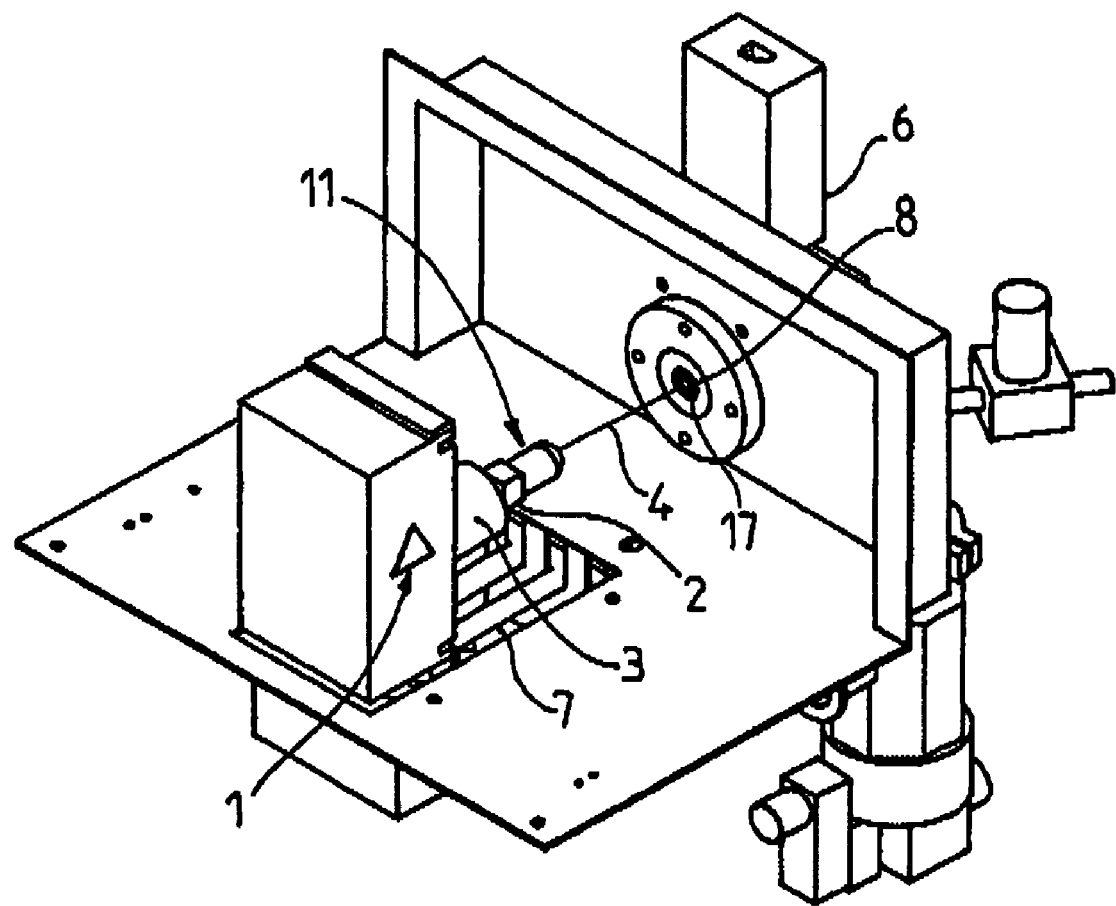
FIG. 1 is a schematic representation of the device for positioning a sample, according to the invention.

FIG. 1 shows the device for positioning a sample according to the invention. It includes a protective member 1 of a mechanic assembly which comprises a cutting tool 2. By cutting tool is meant any rotary sharp tool such as drill bits, milling cutters for instance, or sanding implements such as, for instance, sanding heads. According to a preferred embodiment, the mechanic assembly includes means for driving 3 said cutting tool 2. The protective member 1 may for instance be a casing and the driving means 3 of the cutting tool 2 comprise a motor and a piston. Said driving means 3 and the cutting tool 2 delineate an axis 4 centered on first electrode means 5, of inner diameter D (typically between 1 and 8 mm), of a glow discharge spectrometer 6.

According to an embodiment, the protective member 1 is installed on rails 7 and is susceptible to slide or roll between two end positions, a retracted position and a forward position. The forward position corresponds to the cutting tool 2 inserted deepest in the first electrode means 6. A sample 8 may be mounted on the spectrometer 6 for analysis purposes. The sample 8 includes a first face 9 and a second face 10. The first face 9 is the one liable to be exposed partially to a glow discharge created in the spectrometer 8 and the second face 10 is external to said spectrometer 6 and opposite the mechanic assembly. The first electrode means 5 include according to a preferred embodiment an anode.

The device comprises a detachable arm 11 having an aperture 12 at its end of diameter d' and having a main axis 13 centered on the first electrode means 5. The arm 11 is according to an embodiment made of Teflon. Such a detachable arm 11 includes a light source 14 generating a light beam centered on said first electrode means 5. The diameter d of the light beam is substantially equal to the inner diameter D of the first electrode means 5. Advantageously, the variation amplitude of the d/D ratio remains smaller than to ten percent. The diameter d of the light beam may be controlled by means of a flow restrictor. According to an advantageous embodiment, the light source 14 is a laser diode. It is power supplied by an external electric power supply unit 15. The diameter d' is advantageously at least equal to the inner diameter D of the first electrode means 5 in order to let through the light beam. In a first embodiment, the arm 11 is positioned on the cutting tool 2. In a second embodiment it is positioned on the driving means 3, the cutting tool 2 having being disinstalled previously.

Figure 2:
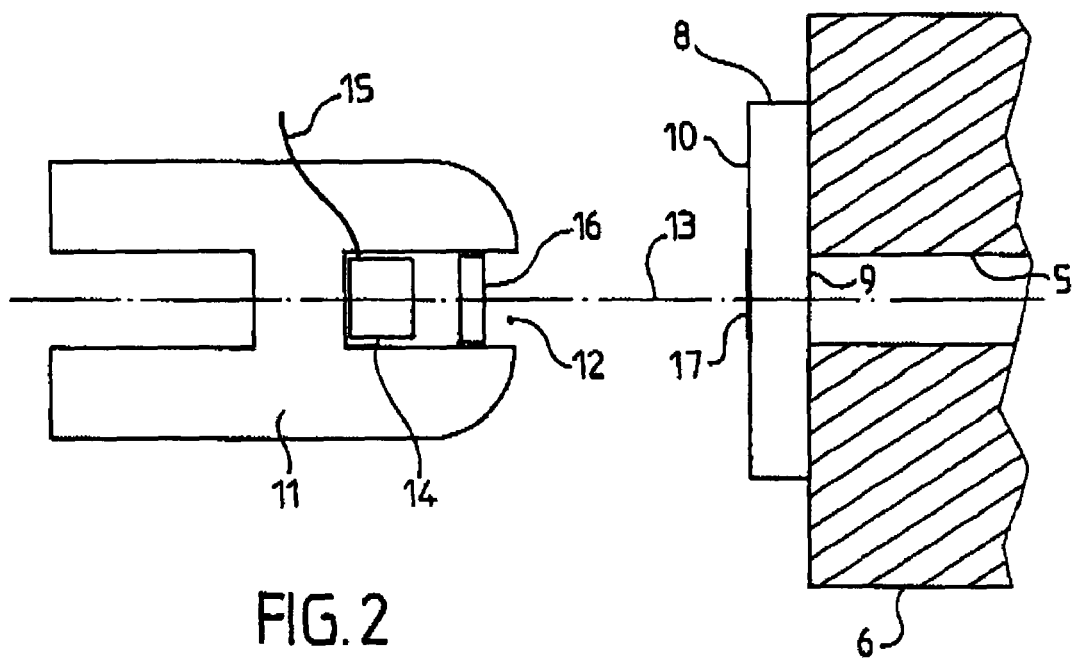
FIG. 2 is a schematic representation of the detachable arm with the light source inserted along the main axis of the arm.
Figure 3:
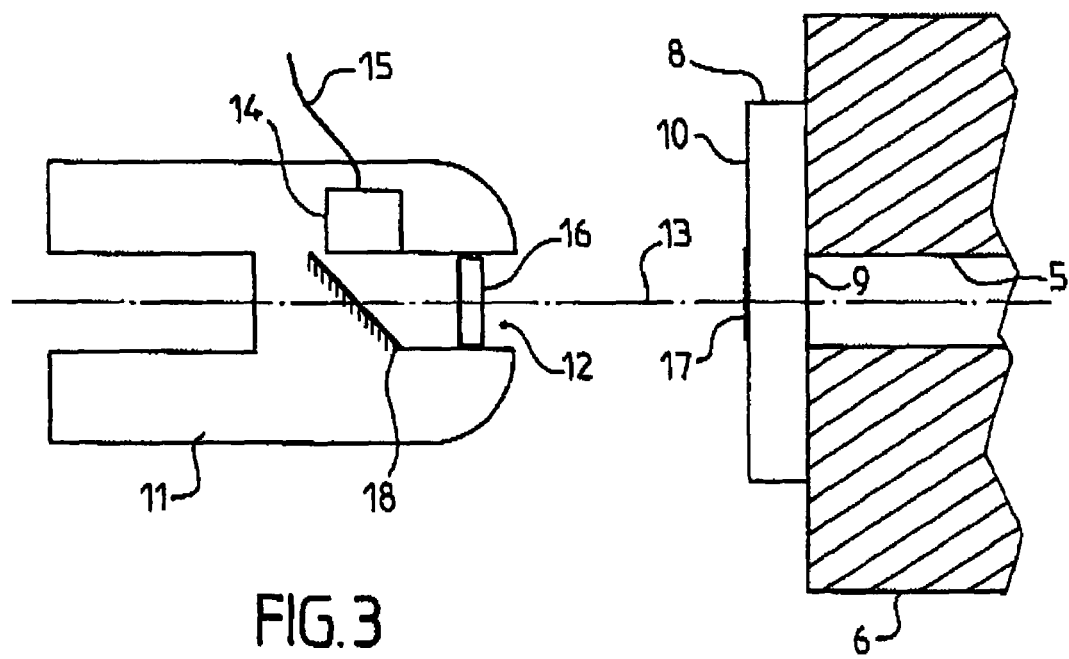
FIG. 3 represents the detachable arm with the light source located perpendicular to the main axis of the arm.

In a first embodiment (cf. FIG. 2), the light source 14 is inserted along the main axis 13 of the detachable arm 11. The arm 11 is fitted with an output optic lens 16 enabling collimation of the luminous beam. Said luminous beam is centered on the first electrode means 5 thereby creating a luminous spot 17 on the outer face 10 of the sample 8 and enabling therefore to track precisely the portion of the first face 9 which will be exposed effectively to the glow discharge. It is thus possible to locate on the second face 10 of the sample 8 and therefore externally, said portion. In a second embodiment (cf. FIG. 3), the light source 14 is located perpendicular to the main axis 13 of the arm 11. The later comprises therefore means 18 for reflecting the light beam to the first electrode means 5. Advantageously, said means 18 include a plane mirror positioned at 45° relative to the main axis 13 of the detachable arm 11 between the light source 14 and the output of the arm 11. The arm 11 is fitted with an output optic lens 16 enabling collimation of the light beam from the light source 14.

The invention also relates to a method for positioning a sample 8 wherein a sample 8 to be analysed is mounted against first electrode means 5 of a glow discharge spectrometer 6. According to an embodiment, to do so, the sample 8 is held manually in place against the first electrode means 5 and vacuum is made in the spectrometer 6 using mechanic pumps. Then, a detachable arm 11 is mounted on a mechanic assembly comprising a cutting tool 2, said arm 11 being centered and in the axis of the first electrode means 5. According to an embodiment, the protective member 1 is a casing, the cutting tool 2 comprises a drill bit, for instance.

Finally, said sample 8 is illuminated with a light beam of diameter d substantially equal to the inner diameter D of the first electrode means 5 and the position of the light beam is located on the sample 8. According to a preferred embodiment, the light beam is derived from a laser diode. According to an embodiment, the member 1 is in retracted position and the sample 8 is tracked with the beam. Advantageously, the sample 8 is mounted on an accurate positioning device, for instance, a table X-Y. Recording the positions of zones effectively exposed to the glow discharge then enables to map the structure of the sample 8 using the glow discharge spectrometer 6.

The invention could not be limited to the preceding description and is liable to changes with the evolution of technologies. Substitutions and/or modifications in the general structure in the details of this positioning device may be brought by a man of the art without departing from the framework of this invention.

Thus according to an embodiment, the detachable arm 11 includes a light source 14 generating a luminous beam and an output optic lens 16 focusing said light beam on the first electrode means 5. The luminous spot 17 produced by the light beam on the outer face 10 of the sample 8 has a diameter d" substantially equal to the inner diameter D of the first electrode means 5 and is centered on said means 5.

The invention claimed is:

1. A device for positioning a sample in a glow discharge spectrometer including a protective member of a mechanic assembly, said mechanic assembly including a cutting tool liable to receive a detachable arm having a main axis, said glow discharge spectrometer comprises first electrode means, of inner diameter D, against which a sample to be analysed may be mounted, said sample having a first face and a second face, said first face liable to be exposed partially to a glow discharge created in the spectrometer and the second face being external to said spectrometer and opposite the mechanic assembly, characterised in that:

the detachable arm includes a light source generating a light beam centered on said first electrode means.

2. A device for positioning a sample according to claim 1, characterised in that the light beam has a diameter d substantially equal to the inner diameter D of the first electrode means.

3. A device for positioning a sample according to one of the claims 1 or 2, characterised in that the light source is a laser diode.

4. A device for positioning a sample according to claim 1, characterised in that the light source is situated along the main axis of the arm.

5. A device for positioning a sample according to claim 1, characterised in that the light source is located perpendicular to the main axis of the arm.

6. A device for positioning a sample according to claim 5, characterised in that a plane mirror is inserted in the arm and positioned at 45° of the main axis of the arm.

7. A device for positioning a sample according to claim 1, characterised in that the arm is fitted with an output optic lens.

8. A method for determining a position of a sample in a glow discharge spectrometer comprising:

installing a sample to be analysed against first electrode means of a glow discharge spectrometer, providing a detachable arm on a mechanic assembly, the mechanic assembly comprising a cutting tool, said arm being centered and in an axis of the first electrode means, illuminating said sample with a light beam having a diameter d substantially equal to an inner diameter D of the first electrode means, and providing the position of the luminous beam on the sample on the basis of the illumination of the sample, to a user.

9. A method for positioning a sample according to claim 8, characterised in that a structure of the sample is mapped using the glow discharge spectrometer.

* * * * *

UNITED STATES PATENT AND TRADEMARK OFFICE
CERTIFICATE OF CORRECTION

PATENT NO. : 7,227,635 B2  
APPLICATION NO. : 10/480264  
DATED : June 5, 2007  
INVENTOR(S) : Patrick Chapon Page 1 of 1

It is certified that error appears in the above-identified patent and that said Letters Patent is hereby corrected as shown below:

Title Page

In the Assignee:

Delete "Cabinet Harle & Phelip," and substitute therefor -- JOBIN YVON SAS --.

Signed and Sealed this

Twenty-fifth Day of March, 2008

JON W. DUDAS  
*Director of the United States Patent and Trademark Office*